United States Patent [19]

Shin et al.

[11] Patent Number: 4,691,186
[45] Date of Patent: Sep. 1, 1987

[54] AGING TREATMENT FOR SEMICONDUCTOR GAS SENSOR

[75] Inventors: Yasuo Shin, Nara; Takeshi Tanabe, Higashiosaka, both of Japan

[73] Assignee: Sharp Kabushiki Kaisha, Osaka, Japan

[21] Appl. No.: 255,489

[22] Filed: Apr. 20, 1981

[30] Foreign Application Priority Data

Apr. 25, 1980 [JP]  Japan ................................. 55-56030

[51] Int. Cl.$^4$ .............................................. H01L 7/00
[52] U.S. Cl. ........................................ 338/34; 338/35; 219/10.55 B; 219/10.55 R
[58] Field of Search ................. 338/35, 34; 422/98; 23/232 E; 73/27 R; 324/71 SN; 219/10.55 B, 10.55 R; 436/151; 204/402

[56] References Cited

U.S. PATENT DOCUMENTS

| | | | |
|---|---|---|---|
| 3,644,795 | 2/1972 | Taguchi | 338/34 |
| 3,955,268 | 5/1976 | Chou et al. | 338/34 |
| 4,259,292 | 3/1981 | Ichinose et al. | 338/34 |
| 4,311,895 | 1/1982 | Tanabe | 219/10.55 B |

*Primary Examiner*—E. A. Goldberg
*Assistant Examiner*—C. M. Sigda
*Attorney, Agent, or Firm*—Birch, Stewart, Kolasch & Birch

[57] ABSTRACT

A $SnO_2$ semiconductor gas sensor for use in a cooking apparatus to detect the cooking condition is manufactured through an aging treatment for stabilizing the operation of the $SnO_2$ semiconductor gas sensor. In the aging treatment, the $SnO_2$ semiconductor gas sensor is disposed in a gas ambience including a gas which is developed in the cooking apparatus. More specifically, the gas ambience includes a dimethyl siloxane gas which is developed from a heated silicone compound. The gas ambience in the aging treatment is held at a high temperature, for example, 150° C. through 250° C. to provide the $SnO_2$ semiconductor gas sensor of which the resistance value and sensitivity are stable even in the high temperature ambience when oven cooking is performed by the cooking apparatus.

5 Claims, 13 Drawing Figures

AGING TREATMENT FOR SEMICONDUCTOR GAS SENSOR

BACKGROUND AND SUMMARY OF THE INVENTION

The present invention relates to an aging treatment for stabilizing an operation of a $SnO_2$ semiconductor gas sensor.

The $SnO_2$ semiconductor gas sensor detects the gas concentration through the use of the variation of the electric conductivity due to the chemical adsorption of a reducing gas. The $SnO_2$ semiconductor gas sensor includes a sensor element of the n-type semiconductor sintered material of which the major component is $SnO_2$.

The above-mentioned $SnO_2$ semiconductor, gas sensor is widely used in domestic gas leak alarm devices.

Recently, the present assignee has developed microwave oven model numbers R-5000W and R-5800 which include the above-mentioned $SnO_2$ semiconductor gas sensor, typically a Figaro Gas Sensor TGS#812 or TGS#813 manufactured by Figaro Engineering Inc., for controlling a cooking operation. In this microwave oven, the oven cooking and the grill cooking are conducted by a sheath heater disposed in an oven cavity, and the microwave cooking is conducted through the use of a microwave energy of 2,450 MHz derived from a magnetron. The cooking control is automatically conducted through the use of an output signal derived from the gas sensor once the operator actuates a desired cooking command switch.

A typical control circuit of the above-mentioned microwave oven is described in copending U.S. patent application Ser. No. 71,179, COOKING UTENSIL CONTROLLED BY GAS SENSOR OUTPUT, filed on Aug. 31, 1979 now U.S. Pat. No. 4,311,895, by Takeshi Tanabe and assigned to the same assignee as the present application. The British counterpart was published on Aug. 28, 1980 and bears a publication number 2,040,502 The German counterpart is DOS No. 2,935,862.

To perform reliable cooking control, the gas sensor must operate stably. However, the conventional gas sensor shows a remarkable variation in its detection characteristics. Further, the conventional gas sensor manufacturing method is not suited for mass production.

Accordingly, an object of the present invention is to stabilize an operation mode of a $SnO_2$ semiconductor gas sensor when it is used in a microwave oven.

Another object of the present invention is to provide a novel aging treatment for stabilizing the operation of a $SnO_2$ semiconductor gas sensor.

Still another object of the present invention is to provide an aging treatment of a $SnO_2$ semiconductor gas sensor suited for mass production.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a $SnO_2$ semiconductor gas sensor is treated to age in a gas ambience including a gas component which is generated in an apparatus in which the $SnO_2$ semiconductor gas sensor is desired to be installed.

In a preferred form, to provide a $SnO_2$ semiconductor gas sensor to be used in a microwave oven, the $SnO_2$ semiconductor gas sensor is aged in a dimethyl siloxane gas ambience, the dimethyl siloxane being developed from a heated silicon compound. The aging period is thirty minutes through two hours. In another preferred form, the dimethyl siloxane gas ambience is held at a high temperature, for example, 150° C. to 250° C.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
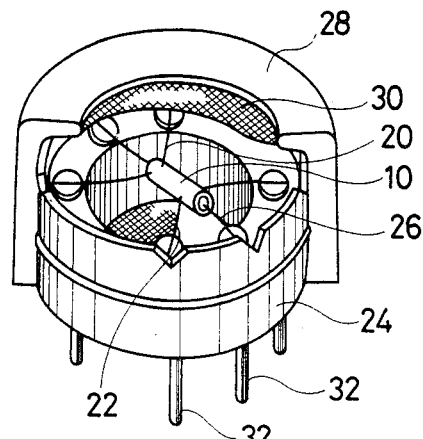
FIG. 1 is a partially cut away perspective view of a $SnO_2$ semiconductor gas sensor.
Figure 2:
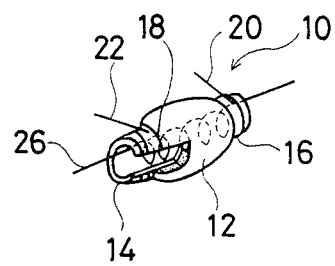
FIG. 2 is a partially cut away perspective view of a sensor element included in the $SnO_2$ semiconductor gas sensor of FIG. 1.

In FIGS. 1 and 2, a SnO$_2$ semiconductor gas sensor includes a sensor element 10 comprising a sintered member 12 of which the major component is SnO$_2$. The sintered member 12 is supported by a ceramic pipe 14 on which a pair of electrodes 16 and 18 are formed. A pair of sensor lead wires 20 and 22 are fixed to the pair of electrodes 16 and 18, and the sensor element 10 is disposed in a resin block 24 via the pair of sensor lead wires 20 and 22. A heater coil 26 is disposed in the ceramic pipe 14 in order to warm the sintered member 12, thereby ensuring a stable detection. The resin block 24 is covered by a cover 28 including a gauze 30. An input/output socket 32 is secured to the resin block 24 to connect the sensor element 10 to a control circuit.

Figure 3:
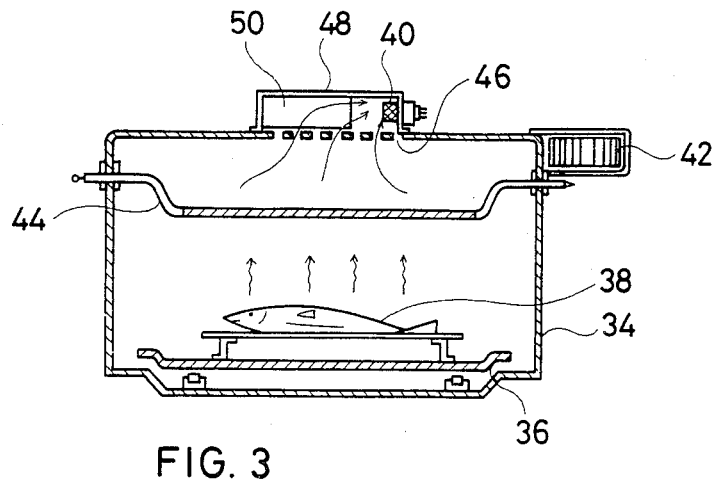
FIG. 3 is a sectional view of a cooking apparatus employing the $SnO_2$ semiconductor gas sensor of FIG. 1.

FIG. 3 shows a cooking apparatus including the above constructed SnO$_2$ semiconductor gas sensor (40). The cooking apparatus includes an oven cavity 34 and a tray 36 for supporting a foodstuff 38 to be cooked. The SnO$_2$ semiconductor gas sensor 40 is disposed above the oven cavity 34 to detect the concentration of a gas generated from the foodstuff 38. The microwave cooking is performed by the microwave energy generated by a magnetron (not shown) disposed at the outside of the oven cavity 34. A cooling fan 42 is provided to cool the magnetron. A sheath heater 44 is disposed at an upper section of the oven cavity 34 in order to cook the foodstuff 38 through the use of the radiation heat. The air flow created by the cooling fan 42 is introduced into the oven cavity 34 for discharging the moisture and gas generated from the foodstuff 38. More specifically, an exhaustion aperture 46 comprising a plurality of openings is formed in the ceiling wall of the oven cavity 34. The moisture and gas are effectively discharged through the exhaustion aperture 46 by the forced air flow created by the cooling fan 42. An exhaustion duct 48 is disposed above the oven cavity 34 to confront the exhaustion aperture 46. The SnO$_2$ semiconductor gas sensor 40 is disposed in the exhaustion duct 48. A deflection plate 50 is disposed in the exhaustion duct 48 to effectively supply the exhaustion gas toward the SnO$_2$ semiconductor gas sensor 40.

An operation mode of the above constructed cooking apparatus is described in the copending U.S. Pat. No. 4,311,895, entitled COOKING UTENSIL CONTROLLED BY GAS SENSOR OUTPUT, filed on Aug. 31, 1979 by Takeshi Tanabe and assigned to the same assignee as the present application.

Attention should be directed to the following facts when the above-mentioned SnO$_2$ semiconductor gas sensor is used in a cooking apparatus to control the cooking operation.

Figure 4:
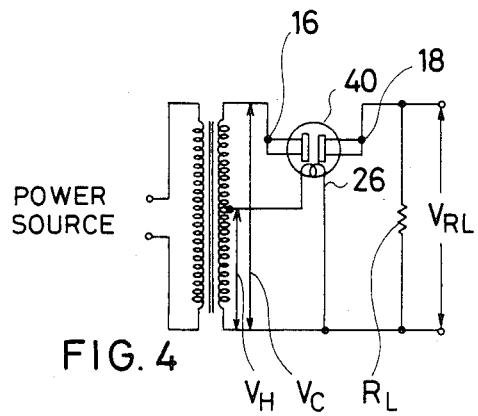
FIG. 4 is a circuit diagram of a detection circuit connected to the $SnO_2$ semiconductor gas sensor of FIG. 1.
Figure 5:
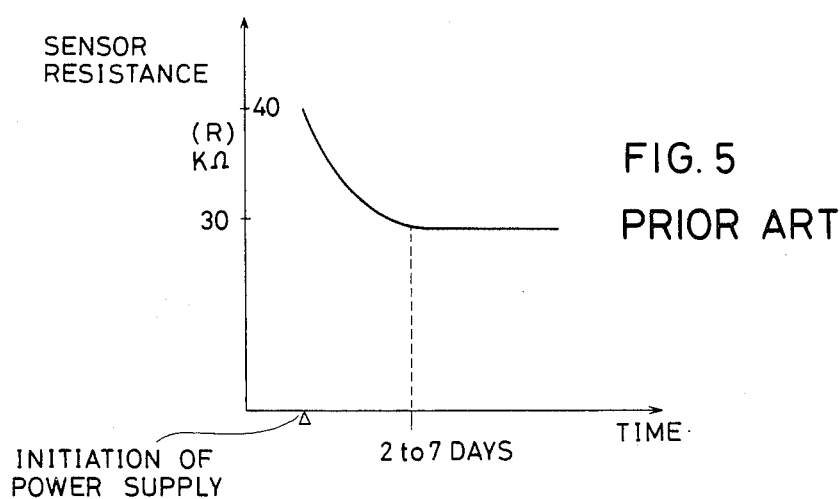
FIG. 5 is a graph showing the sensor element resistance variation due to time elapse in a $SnO_2$ semiconductor gas sensor of the prior art.

(1) Sensor Resistance Variation When the Gas Sensor is First Supplied with Power FIG. 4 shows a detection circuit for detecting a variation of the sensor resistance. Like elements corresponding to those of FIG. 2 are indicated by like numerals. FIG. 5 shows the detection result when the SnO$_2$ semiconductor gas sensor of prior art is used as a sample. It will be clear from FIG. 5 that the sensor resistance does not become stable until two through seven days have passed after the initiation of power supply to the gas sensor 40. This means that the gas sensor of prior art must be tested for two through seven days before the gas sensor shows a stable operation. Thus, the conventional gas sensor is not suited for mass production. In the detection circuit of FIG. 4, the detection condition is as follows:

drive voltage $V_c = 10V$;
heater voltage $V_H = 5V$; and
load resistor $R_L = 4K\Omega$ (2) Influence Caused By a No-Load Operation of a Cooking Apparatus In order to stabilize the operation of the cooking apparatus of FIG. 3, it is required, before the actual cooking operation, to energize the sheath heater 44 without load to conduct the no-load operation (250° C. for 30 minutes). During the no-load operation, the silicone rubber products employed in the cooking apparatus, such as a duct packing, a choke cover and a gas sensor packing, are heated up to a high temperature to develop a dimethyl siloxane gas.

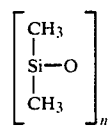

Figure 6:
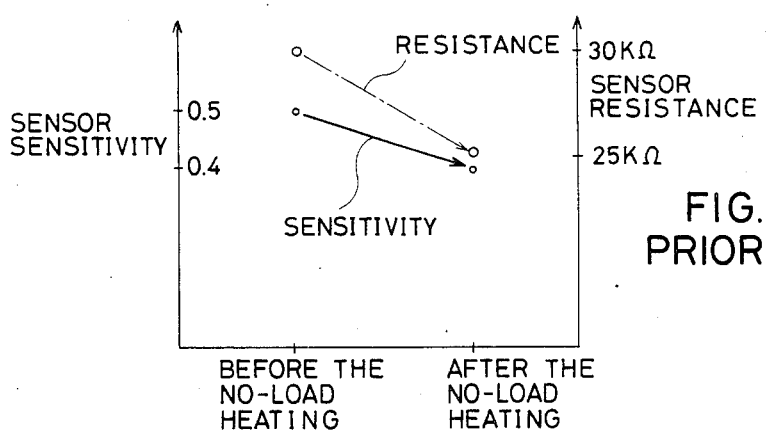
FIG. 6 is a graph showing the sensor element resistance variation and the sensor element sensitivity variation due to a no-load heating of a cooking apparatus when a $SnO_2$ semiconductor gas sensor of prior art is employed.

FIG. 6 shows the variation of the sensor resistance and the sensor sensitivity when the SnO$_2$ semiconductor gas sensor of prior art is made contact with the dimethyl siloxane gas. These variations are the irreversible change and affect on an accurate detection of the cooking condition.

The sensitivity ($\beta$) is detected through the use of the following equation.

$$\beta = R_1/R_0$$

where:
$R_0$ is a sensor resistance when the gas sensor is exposed to a preselected gas of $A_0$ ppm; and
$R_1$ is a sensor resistance when the gas sensor is exposed to the preselected gas of $A_0 \times 60$ ppm. The preselected gas is methane, isobutane or ethanol.

(3) Influence Caused By a High Temperature Ambience

In the grill cooking mode or the oven cooking mode, the sheath heater 44 is energized and, therefore, the SnO$_2$ semiconductor gas sensor 40 disposed near the exhaustion aperture 46 is exposed to a high temperature ambience. In the SnO$_2$ semiconductor gas sensor of prior art, the sensor resistance irreversibly changes due to the high temperature around 150° C. through 250° C. This will cause a deviation in the accurate detection of the cooking condition.

(4) Nonuniformity in Manufacture

Figure 7:
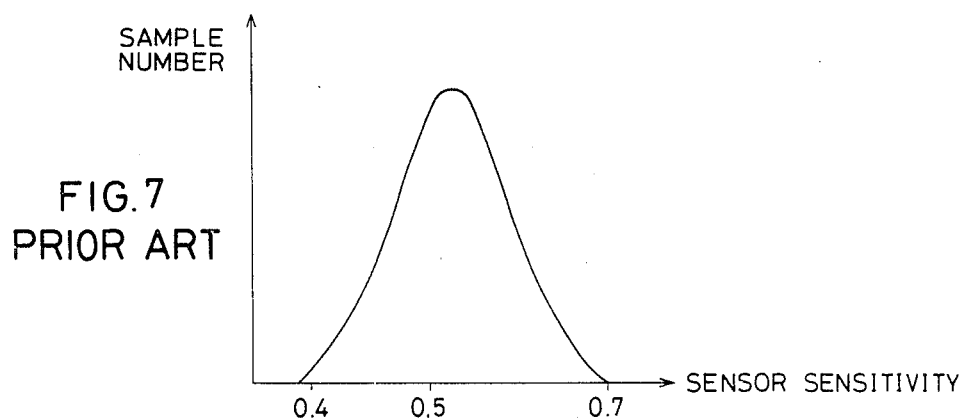
FIG. 7 is a graph showing sensor sensitivity distribution of a $SnO_2$ semiconductor gas sensor manufactured by the conventional method.

The SnO$_2$ semiconductor gas sensor manufactured by the conventional method shows the distribution as shown in FIG. 7 in the sensitivity. This wide distribution is not suited for providing a cooking control system of an accurate operation.

The present invention is to provide a novel aging treatment to minimize the above-mentioned defects and to form a SnO$_2$ semiconductor gas sensor suited for controlling the cooking operation in a cooking apparatus.

Figure 8:
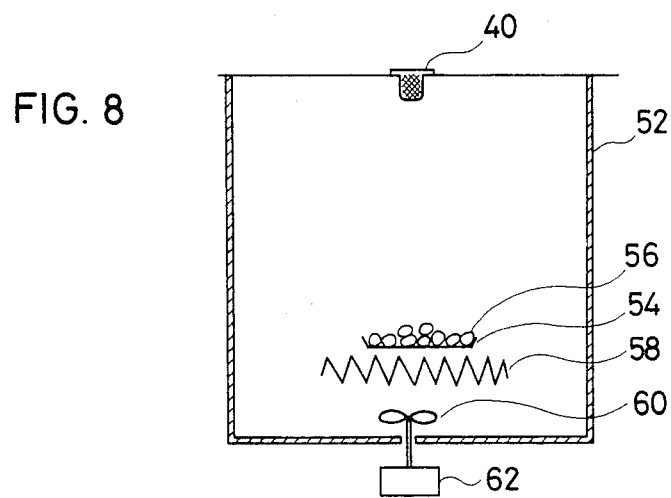
FIG. 8 is a schematic sectional view of an embodiment of an aging apparatus for performing an aging treatment of the present invention.

FIG. 8 schematically shows an aging apparatus for conducting an aging treatment to the SnO$_2$ semiconductor gas sensor 40. The aging apparatus includes a gas chamber 52. A tray 54 is disposed in the gas chamber 52 for supporting a silicone compound 56. A heater 58 is disposed below the tray 54 to heat up the silicone compound 56, thereby generating the dimethyl siloxane gas. The thus generated dimethyl siloxane gas is effectively applied to the $SnO_2$ semiconductor gas sensor 40 through the use of a stirring fan 60 activated by a motor 62. The $SnO_2$ semiconductor gas sensor 40 is inserted into the ceiling wall of the gas chamber 52 so that the sensor element is exposed to the dimethyl siloxane gas generated in the gas chamber 52.

The heater 58 functions not only to heat up the silicone compound 56 for generating the dimethyl siloxane gas but also to heat up the ambience in the gas chamber 52 to 150° C. through 250° C. The aging treatment is conducted for thirty minutes through two hours. During the aging treatment, the $SnO_2$ semiconductor gas sensor 40 is supplied with power ($V_c = 10V$ and $V_H = 5V$) to be placed in the operative condition.

The $SnO_2$ semiconductor gas sensor treated by the above-mentioned aging method shows the following characteristics.

Figure 9:
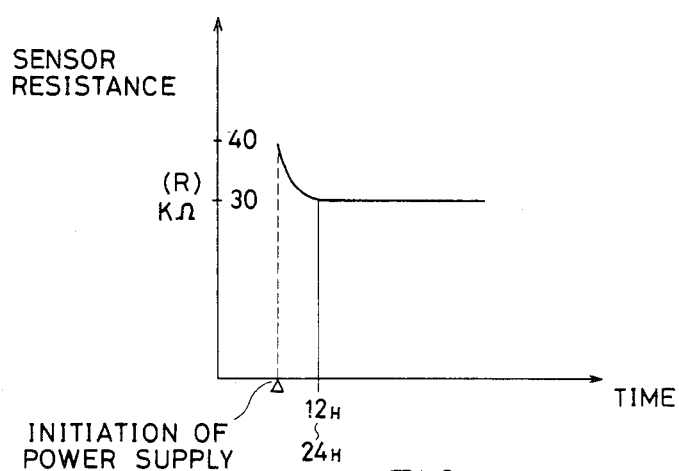
FIG. 9 is a graph showing the sensor element resistance variation due to time elapse in a $SnO_2$ semiconductor gas sensor treated by an aging method of the present invention.
Figure 11:
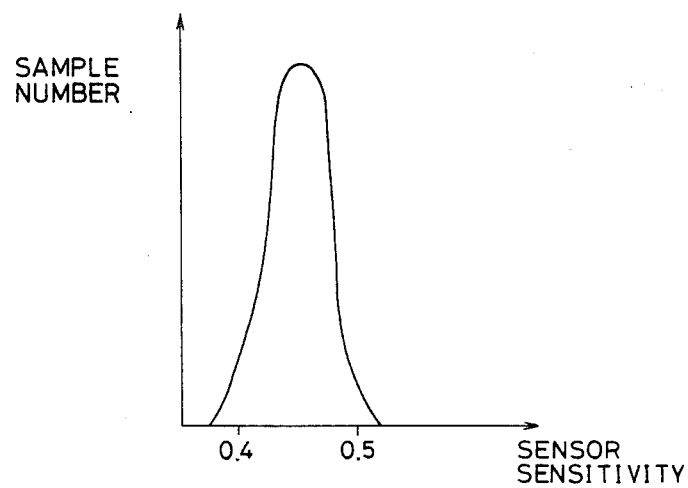
FIG. 11 is a graph showing sensor sensitivity distribution of a $SnO_2$ semiconductor gas sensor manufactured through the aging treatment of the present invention.

(I) Sensor Resistance Variation When the Gas Sensor is First Supplied with Power It will be clear from FIG. 9 that the $SnO_2$ semiconductor gas sensor manufactured by the aging treatment of the present invention stabilizes the resistance value in twelve hours through one day. Thus, the characteristics check of the gas sensor can be conducted after 12 through 24 hour power supply. Accordingly, the present aging treatment facilitates the mass production of the $SnO_2$ semiconductor gas sensor. FIG. 11 shows the sensor sensitivity distribution of the $SnO_2$ semiconductor gas sensor manufactured through the aging treatment of the present invention. The distribution is narrow as compared with the distribution of the gas sensor manufactured by the prior art method shown in FIG. 7. Therefore, an accurate cooking control is ensured when the $SnO_2$ semiconductor gas sensor treated by the aging method of the present invention is employed in a cooking apparatus.

(II) Influence Caused By a No-Load Operation of a Cooking Apparatus

Figure 10:
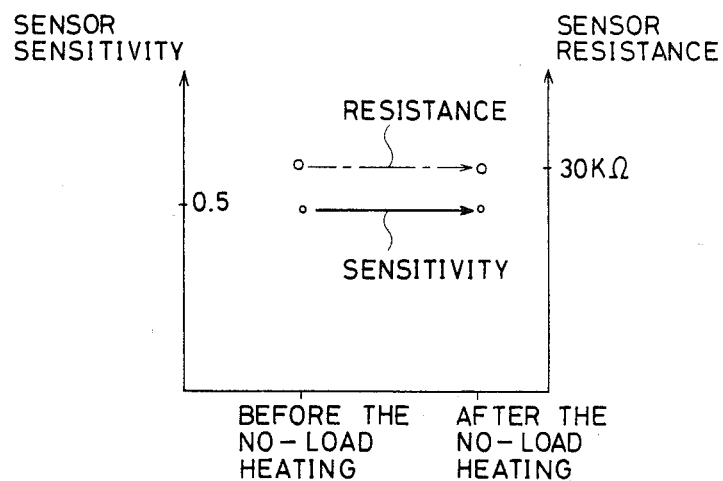
FIG. 10 is a graph showing the sensor element resistance stability and the sensor element sensitivity stability against a no-load heating of a cooking apparatus when a $SnO_2$ semiconductor gas sensor manufactured through an aging treatment of the present invention is employed.
Figure 12:
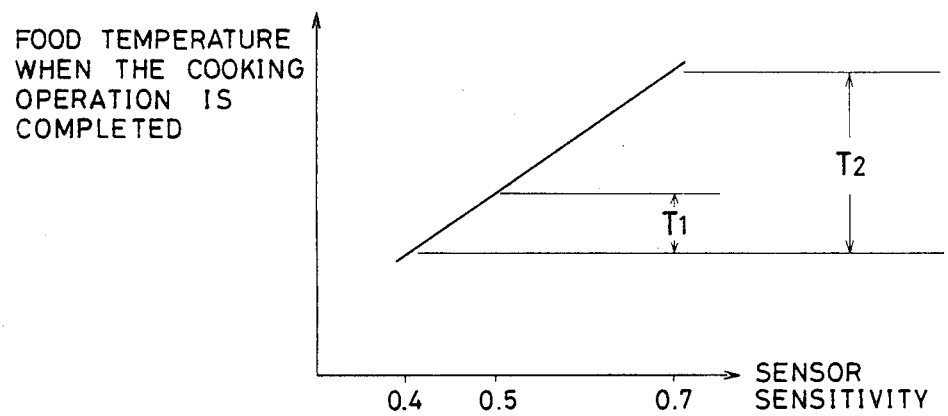
FIG. 12 is a graph showing a relationship between the sensor sensitivity difference and the food temperature difference when the cooking operation is completed.

The $SnO_2$ semiconductor gas sensor manufactured through the aging treatment of the present invention is stable in the sensor resistance and the sensitivity even when the dimethyl siloxane gas is applied thereto as shown in FIG. 10. This ensures a stable detection of the cooking condition. FIG. 12 shows the relationship between the sensor sensitivity and the food temperature when the cooking operation is completed. The conventional $SnO_2$ semiconductor gas sensor sensitivity is distributed between 0.4 and 0.7 as shown in FIG. 7 and, therefore, the cooking completion temperature has a wide range $T_2$ shown in FIG. 12. Contrarily, the $SnO_2$ semiconductor gas sensor manufactured through the aging treatment of the present invention has the sensor sensitivity between 0.4 and 0.5 as shown in FIG. 11 and, therefore, the cooking completion temperature is limited within a range $T_1$ shown in FIG. 12. Thus, the cooking operation of an accurate control is achieved.

(III) Influence Caused By a High Temperature Ambience

Figure 13:
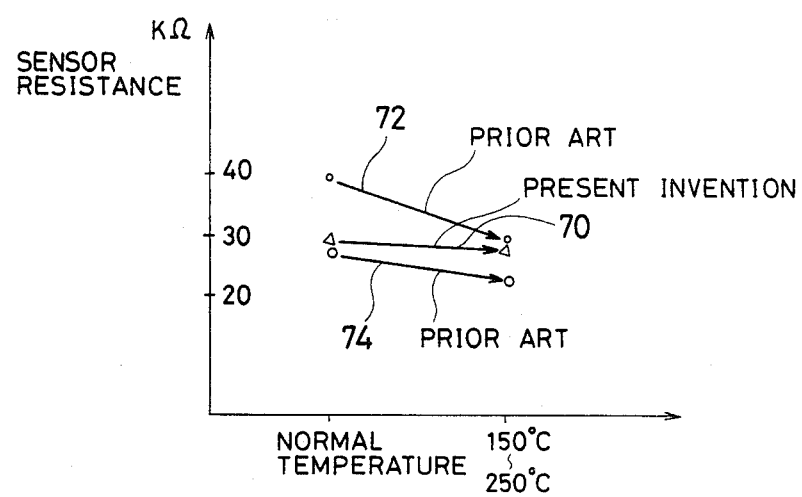
FIG. 13 is a graph showing a comparative test result of a sensor resistance variation between the conventional gas sensor and the gas sensor manufactured through the aging treatment of the present invention, under a high temperature ambience.

The $SnO_2$ semiconductor gas sensor manufactured through the aging treatment of the present invention does not vary the sensor resistance even in a high temperature ambience as shown by a line 70 in FIG. 13. As already discussed, the $SnO_2$ semiconductor gas sensor of prior art changes the sensor resistance in a high temperature ambience as shown by lines 72 and 74 in FIG. 13. It will be clear from FIG. 13 that the $SnO_2$ semiconductor gas sensor manufactured through the aging treatment of the present invention ensures a stable operation even in a high temperature ambience such as in the oven cooking mode.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method for stabilizing the operation of a gas sensor prior to its being installed in a cooking apparatus for detecting the cooking condition performed therein which comprises
    aging a $SnO_2$ semiconductor gas sensor by disposing said $SnO_2$ semiconductor gas sensor in an aging chamber having a gas ambience including a gas which is developed in an apparatus in which said $SnO_2$ semiconductor gas sensor is desired to be installed, said gas sensor being disposed in said gas ambience for a sufficient time and at a gas ambience temperature which is effective in achieving said stability of operation; and
    installing said aged $SnO_2$ semiconductor gas sensor in a cooking apparatus.

2. The aging treatment of claim 1, wherein said gas ambience includes dimethyl siloxane gas which is generated from a heated silicone compound selected from the group consisting of a silicone oil, a silicone rubber and a silicone resin.

3. The aging treatment of claim 1 or 2, wherein said gas ambience is held at a high temperature.

4. The aging treatment of claim 3, wherein said gas ambience temperature is 150° C. through 250° C.

5. The aging treatment of claim 4, wherein said $SnO_2$ semiconductor gas sensor is disposed in said gas ambience for thirty minutes through two hours.

* * * * *